United States Patent [19]
Feickert

[11] Patent Number: 5,528,142
[45] Date of Patent: Jun. 18, 1996

[54] RESONANT EDDY ANALYSIS- A CONTACTLESS, INDUCTIVE METHOD FOR DERIVING QUANTITATIVE INFORMATION ABOUT THE CONDUCTIVITY AND PERMEABILITY OF A TEST SAMPLE

[76] Inventor: Carl A. Feickert, 1205 Devonshire Dr., Champaign, Ill. 61821

[21] Appl. No.: 491,771

[22] Filed: Jun. 19, 1995

[51] Int. Cl.$^6$ .......................... G01N 27/72; G01R 33/12
[52] U.S. Cl. .............................. 324/236; 324/708
[58] Field of Search ................................. 324/236, 708, 324/308, 310, 234, 228, 262, 655

[56] References Cited

U.S. PATENT DOCUMENTS

| | | | |
|---|---|---|---|
| 3,609,580 | 9/1971 | Thompson | 324/236 |
| 3,719,882 | 3/1973 | Pincus | 324/236 |
| 3,931,571 | 1/1976 | Hocking et al. | 324/236 |
| 4,000,458 | 12/1976 | Miller et al. | 324/236 |
| 4,182,986 | 1/1980 | Parker | 324/236 |
| 4,230,987 | 10/1980 | Mordwinkin | 324/236 |
| 4,353,027 | 10/1982 | Ballato et al. | 324/708 |
| 4,387,338 | 6/1983 | Hecht et al. | 324/236 |
| 4,678,994 | 7/1987 | Davies | 324/236 |
| 4,797,614 | 1/1989 | Nelson | 324/236 |
| 4,835,471 | 5/1989 | Kutilin | 324/236 |
| 4,922,201 | 5/1990 | Vernon | 324/236 |
| 5,119,022 | 6/1992 | Kranbuehl et al. | 324/236 |
| 5,142,228 | 8/1992 | Kingsbury | 324/236 |
| 5,273,151 | 12/1993 | Carmen et al. | 324/236 |
| 5,394,084 | 2/1995 | Snyder | 324/236 |

*Primary Examiner*—Walter E. Snow

[57] ABSTRACT

A method for quantifying the permeability or conductivity of a conducting material, comprises the steps of providing a circuit including an inductor with a coil and a capacitor connected in parallel to the inductor, the coil having an interior space adapted to enclose the sample material therein; inserting the sample material into the interior space of the coil to completely enclose the sample material therein; resonating the circuit with the capacitor with capacitance C' with the inserted sample material at a resonant frequency $f_0$ and measuring the resulting impedance, Z' of the circuit; measuring the impedance of the loaded circuit at various frequencies above and below the resonant frequency $f_0$, and plotting a first bell-shaped curve from the measured impedances against frequencies; resonating the circuit with the capacitor with capacitance C' at a resonant frequency $f_x$ with the sample material removed from the coil and measuring the resulting impedance, $Z_0$; measuring the impedance of the empty circuit at various frequencies above and below the resonant frequency $f_x$, and plotting a second bell-shaped curve of the measured impedances against frequencies; and determining the conductivity or permeability of the sample material from the first and second bell-shaped curves.

4 Claims, 1 Drawing Sheet

5,528,142

RESONANT EDDY ANALYSIS- A CONTACTLESS, INDUCTIVE METHOD FOR DERIVING QUANTITATIVE INFORMATION ABOUT THE CONDUCTIVITY AND PERMEABILITY OF A TEST SAMPLE

FIELD OF THE INVENTION

The present invention relates in general to a method for determining the conductivity and permeability of a conducting sample material at various frequencies and in particular to a method that relies on a RLC electrical circuit that is resonated with and without the sample material inserted into a coiled inductor wherein the changes in the circuit parameters at resonance are related to the material's conductivity and permeability.

BACKGROUND OF THE INVENTION

The conductivity and permeability of certain materials at the DC level are well known. However, in a materials development research program, it is often necessary to have knowledge of a material's conductivity and permeability at certain frequencies, for example, radio frequencies. For example, in designing an effective shielding system, one needs to know the conductivity and permeability of the material under consideration under various frequencies that would be typically encountered. Generally, the higher the values of the conductivity and permeability of the material, the better it would be as a shielding element.

Prior art methods typically require large samples, which may not be available in an initial exploratory program. The traditional measure of material conductivities relies on some variant of the standard "4-probe" D.C. measurement. This determination alone is not a sufficient measure of electrical conductivity, in that the intrinsic A.C. reactance (capacitive and inductive) of any material sample is not observed by this measurement, but does have a crucial bearing on the A.C. values of these parameters. These reactive components arise quite naturally in any conductive composite as electrical manifestations of the discrete aggregate (capacitive reactance) and interconnecting filaments (resistive and inductive reactance). It is generally not possible to accurately measure these material parameters, at the frequencies of interest, using any A.C. bridge technique that makes physical contact with the test sample, because of the intrinsic parasitic reactance of the test leads.

The traditional measure of material conductivities relies on some variant of the standard "4-probe" D.C. measurement, and variants of the "Rowland Ring" for permeabilities. Indirect inductive methods are similar to Vernon et al., U.S. Pat. No. 4,922,201.

In Vernon, there exists a number of limitations and or disadvantages which include but not necessarily limited to the following: 1) The problem of coupling (the so-called "lift-off") and the associated sensitivity between the sensing probe and material to be tested; see DTIC publication ADA189823, pages 14–17. 2) The thickness of the sample can be a consideration in the method of Vernon et al. and results in the reliance on empirical relationships to deal with samples of arbitrary thickness. 3) The inductance of the probe must have increased no more than 4% above its minimum value; and there must be no frequency dependent shielding effects; see Vernon, column 4, lines 24–30 and equation 1; column 6, equation 5. 4) Vernon deals with skin depths which assume that the sample material has a permeability of free space; this feature and the empirical nature of equations 1 and 5, can limit the utility of their procedure; see equation 2 of the patent. 5) Finally, the method of Vernon et al. has the practical restriction that the probe size and frequency combination be limited such that the observed parameter be constrained between 0.8 and 6 inclusive in order to reduce the errors in subsequent computed quantities to an acceptable level; see column 5, lines 10–14 of the patent.

There is therefore a need to provide a method for measuring the conductivity and permeability of a material at various frequencies without the shortcomings of the prior art.

OBJECTS AND SUMMARY OF THE INVENTION

It is an object of the present invention to provide a method for the analytic and numerical quantification of a material's conductivity and permeability, in terms of readily observed measurement.

It is another object of the present invention to provide a method for measuring a material's conductivity and permeability with a simple contactless, inductive measurement for arbitrary A.C. frequencies ranging between several Kilo Hertz to around 100 Mega Hertz.

It is still another object of the present invention to provide a method for measuring a material's conductivity and permeability that is contactless and is therefor not subject to the intrinsic parasitic reactance of the leads necessarily required in any A.C. bridge technique that make physical contact with a test sample.

It is yet another of the present invention to provide a method for measuring a material's conductivity and permeability that provides a relatively efficient alternative to the traditional resistive methods, which are labor intensive and time consuming.

It is another object of the present invention to provide a method for measuring a material's conductivity and permeability that can accommodate a significant sample volume and thereby provide a more accurate measure of a composite samplers bulk electromagnetic parameters.

It is an object of the present invention to provide a method for measuring material's conductivity and permeability that is relatively inexpensive, requiring only an inductor, several capacitors and an impedance meter.

It is another object of the present invention to provide a method for measuring a material's conductivity and permeability wherein measurements can be preformed at a number of frequencies and thus afford access to frequency dependent features of a test sample.

It is still another object of the present invention to provide a method for measuring a material's conductivity and permeability that has a relatively intrinsic sensitivity, which can be maximized by configuring the inductor tightly about a given sample.

It is still another object of the present invention to provide a method for measuring a material's conductivity and permeability, where the values are derived from directly measured experimental data and classical EM field theory, requiring no adjustable parameters or normalization procedures.

It is another object of the present invention to provide a method for measuring a material's conductivity and permeability that do not require the conducting regions of a given sample to be in contiguous contact.

In summary, the present invention provides a method for quantifying the conductivity or permeability of a conducting sample material at certain frequency, comprising the steps of providing a circuit including an inductor with a coil and a capacitor connected in parallel to the inductor, the coil having an interior space adapted to enclose the sample material therein; inserting the sample material into the interior space of the coil to completely enclose the sample material therein; resonating the circuit with the capacitor with capacitance C' with the inserted sample material at a resonant frequency $f_0$ and measuring the resulting impedance, Z' of the circuit; measuring the impedance of the loaded circuit at various frequencies above and below the resonant frequency $f_0$, and plotting a first bell-shaped curve from the measured impedances against frequencies; resonating the circuit with the capacitor with capacitance C' at a resonant frequency $f_x$ with the sample material removed from the coil and measuring the resulting impedance, $Z_0$; measuring the impedance of the empty circuit at various frequencies above and below the resonant frequency $f_x$, and plotting a second bell-shaped curve of the measured impedances against frequencies; and determining the conductivity or permeability of the sample material from the first and second bell-shaped curves.

These and other objects of the present invention will become apparent from the following detailed description.

BRIEF DESCRIPTIONS OF THE DRAWINGS

DETAILED DESCRIPTION OF THE INVENTION

Figure 1A:
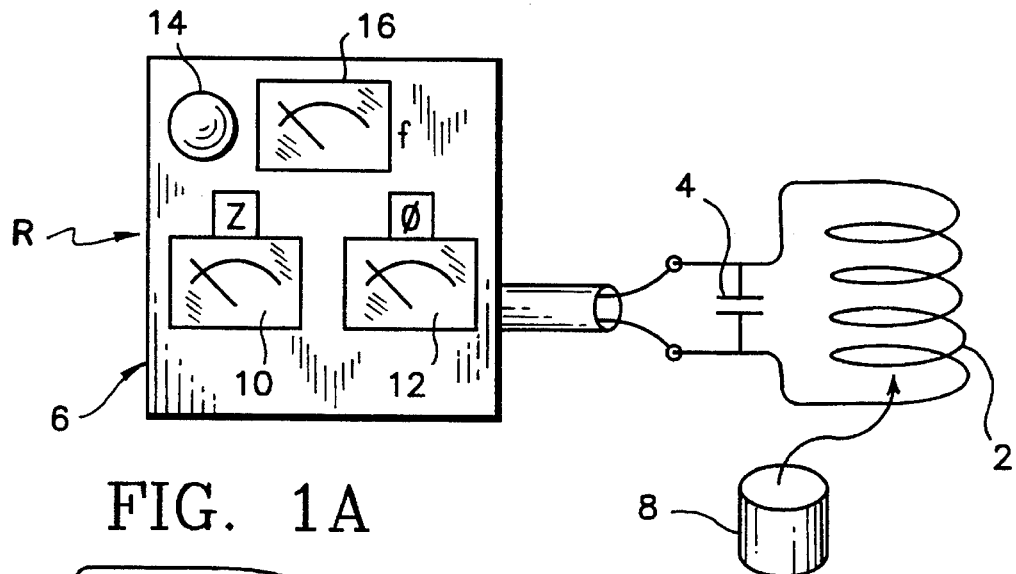
FIG. 1A is schematic diagram of an apparatus used in accordance with the present invention, showing an impedance meter connected to an LC circuit.
Figure 1B:
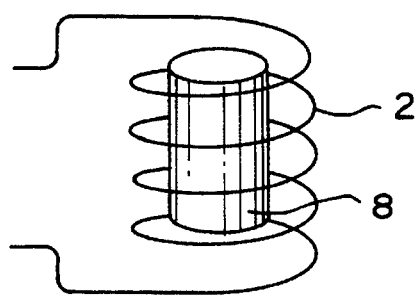
FIG. 1B is a schematic diagram of the inductor of FIG. 1A with the test sample disposed within the coil of the inductor.

An apparatus R used in accordance with the present invention is disclosed in FIG. 1. The apparatus R comprises an inductor 2, a capacitor 4 connected in parallel to the inductor 2 and an impedance meter 6 connected across the capacitor 4 and the inductor 2. The capacitor 4 may be variable. The inductor 2 has a wound coil with an interior space that permits a sample 8 to be placed completely within the interior space of the coil, such that the coil encloses the sample 8, as best shown in FIG. 1B. Since the flux distribution within the coil 2 is generally uniform, locating the sample 8 completely within the coil 2 makes the combination less sensitive to positioning geometry and provides a higher signal to noise (S/N) ratio. Thus, the configuration of the coil of the inductor 2 advantageously maximizes any relative change in the inductance brought about by the insertion of the test sample 8.

The impedance meter 6 has an impedance magnitude indicator 10 and a phase angle magnitude indicator 12. The indicator 12 is advantageously used to tune the circuit at resonance, where the phase angle is zero. The impedance meter also includes an A.C. power supply with variable frequency to drive the LC circuit. A control knob 14 is provided for varying the frequency of this power supply. The output frequency of the impedance meter is shown in a frequency indicator 16.

The inductor 2 may be considered (in some approximation) to have a particular value of inductance depending on the density of flux lines linking the constituent coils. When the conducting test material 8 is inserted within the volume of the inductor 2, the density of the flux lines is modified and observable as appropriate changes in inductance. The impedance meter 6 monitors the changes in the inductor-sample combination by resonating the system with the capacitor 4.

In operation, the sample 8 is placed within the coils of the inductor 2. The winding configuration of the coil maximizes any relative change in inductance brought about by the insertion of the test sample 8. The inductor-sample combination is then resonated with an appropriate capacitor 4 at a given frequency of and the resulting impedance $Z'(f_o)$ and the phase $\phi$ which is normally equal to zero at resonance, are observed using the impedance meter 6. Withdrawing the sample 8 from the inductor 2 and adjusting the capacitor 4 so as to maintain the initial resonant frequency and phase, establishes the empty inductor impedance, $Z_o$. Such a resonant circuit is extremely sensitive to any change in lumped circuit parameters, and manifests such changes as phase-impedance or, equivalently, frequency-impedance deviations. This sensitivity permits the apparatus R to be used for the quantification of the conductivity and permeability of the sample material 8 in terms of these readily observed measurements. For metals the change in capacitance $\Delta C$ (or equivalently in frequency) and the change in impedance, $\Delta Z$, are quantitatively large and distinct. As such, these changes provide a clear signature to the relative merits of the electrodynamic parameters of the sample 8. For materials with more modest parameters, the changes of impedance and frequency turn out to be convoluted in such a way that a more quantitative analyses is required.

Figure 2:
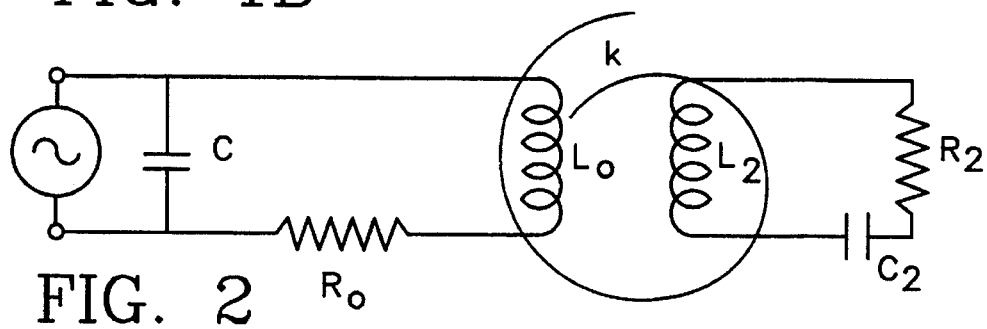
FIG. 2 is a an equivalent circuit of the LC circuit of FIG. 1, with the test material within the inductor coil.

The extraction of electrodynamic parameters in accordance with the present invention requires that the material body be replaced by an equivalent circuit capable of reproducing the essential electrodynamics of the loaded coil. Such a circuit is necessarily inductive and dissipative, with material (and stray external) capacitance. The equivalent circuit is disclosed in FIG. 2, which is essentially a transformer analogy. An A.C. power source is shown connected across the capacitor C. The secondary circuit comprises a secondary coil $L_2$, a capacitor $C_2$ and a resistor $R_2$. The secondary circuit disappears upon removal of the material body from within the coil 2. The choice of parallel or series LRC secondary circuit is somewhat arbitrary, both cases underscoring the feature that the secondary circuit reactive component can change sign. This feature is observed in experiment and theory.

Considering the circuit to the right of the resonating capacitor, C, it is found that the empty $Z_0$ and loaded Z' impedances are respectively, $$Z_o = j\omega L_o + R_o \qquad (1)$$

$$Z' = \left( R_o + \frac{\omega^2 M^2 R_2}{R_2^2 + X_2^2} \right) + j\left( \omega L_o - \frac{\omega^2 M^2 X_2}{R_2^2 + X_2^2} \right) = R' + j\omega L' \qquad (2)$$

where "M" is the mutual inductance, $R_2$ is the equivalent secondary resistance and $X_2$ is the equivalent secondary reactance.

It then follows that $$\frac{\omega(L_0 - L')}{R' - R_0} = \frac{X_2}{R_2} \quad (3)$$

An important feature of the present invention is that measurements of Z and $\omega$ at resonance ($\phi=0°$) significantly increase the S/N ratio and greatly simplifies the circuit algebra. The generic resonance condition for the parallel LRC circuit is, $$Z = \frac{L}{RC} \qquad \omega^2 LC = 1 - \frac{R}{Z} \quad (4)$$

The inductance, L, and resistance, R, are then derivable from the known capacitance, C and measured resonant impedance, Z, and angular frequency, $\omega$. For a given resonant frequency, the $X_2/R_2$ ratio is then expressible in terms of easily measurable parameters:

$$\frac{X_2}{R_2} = \frac{\omega\left(1 - \frac{L'}{L_0}\right) Z_0 C_0}{\frac{Z_0 C_0}{ZC}\left(\frac{L'}{L_0}\right) - 1} \quad (5)$$

$$\frac{L'}{L_0} = \frac{C_0}{C}\left(\frac{\omega^2 + (Z_0 C_0)^{-2}}{\omega^2 + (ZC)^{-2}}\right)$$

To make further progress in the extraction of the electrodynamic parameters from this observable ratio requires the ratio to be modeled in terms of the Maxwell field equations which are sensitive to the analytical dependance of the conductivity, a and permeability, $\mu$ of the test sample. By use of Poynting vector considerations, a first order result for $X_2/R_2$ is derivable which is independent of the detailed inductor-sample geometry, and in certain limits can be expressed in simple closed form. More exacting results are recoverable in higher order (for Equations (6) & (7)) where details of the relative coil-sample geometry become important. For cylindrical samples, the relevant parameter is the ratio of cylinder radius, a(known), to electromagnetic skin depth, $\delta$(unknown).

$X_2/R_2$ is expressible to first order as:

$$\frac{X_2}{R_2} = \left(\frac{\mu_0 a}{\mu \delta} - 1\right) \text{ for } \frac{a}{\delta} > 3.6 \quad (6)$$

and $$\frac{X_2}{R_2} = \frac{4\delta^2}{a^2}\left(\frac{\delta\mu_0}{a\mu} - 1\right) + \frac{a^2}{3\delta^2} \text{ for } \frac{a}{\delta} < 1.05 \quad (7)$$

where $$\delta = \sqrt{\left(\frac{2}{\omega\mu\sigma}\right)} \quad (8)$$

Using standard numerical calculation procedures, one of ordinary skill in the art can calculate $\mu$ and $\sigma$ using equations (6) and (8), or (7) and (8).

The calculations involving equations (6), (7) and (8) to obtain the conductivity and permeability of the test sample can be simplified for certain materials where $\mu=\mu_0$ (permeability of free space). In this case, the permeability $\mu$ is a constant and does not vary with frequency. In another simplifying case, one can take a $\sigma=\sigma_{dc}$ for ferritic materials, such as nickel, cobalt, iron, etc. The conductivity this type of materials have been found to be less dependent on frequency than their permeability. Thus, the method affords access to the frequency dependance, $\mu=\mu(f)$, of the permeabilities of these and similar materials.

The present invention defines a method (at an arbitrary frequency) for the analytic and numerical quantification of a material's conductivity and permeability, in terms of a readily observed measurement (the $X_2/R_2$ ratio). The method is a general interrelationship for arbitrary conductivity and permeability; in many instances, the conductivity is derivable directly from assuming a given permeability (or vise versa). Note that in each limit a frequency exists (i.e., a "$\delta$") such that $X_2/R_2$ is equal to zero, which is in accord with the elemental transformer circuit shown in FIG. 2 above. Observe that for $(\omega L_2 - 1/\omega C_2) > 0$, the inductive portion of the secondary reactance, $X_2$, must dominate. This is referred to as the "inductive limit". For $X_2 < 0$, the capacitive form of the reactance is dominant and referred to as the "capacitive limit". Finally the conductivity, $\sigma$, is generally complex (as is the permeability, $\mu$) and measurements of actual frequency dependence can relate their individual real and imaginary parts by causality (i.e., Kramers-Kronig transformation).

The limiting factor in using the present invention as an inductive method for quantifying a material's conductivity and permeability, is the ability to discern the change of phase and impedance signature that arises after the sample is removed from the inductor. The ability to resolve this signature from any random variations, including temporal changes, is improved by having the sample fill the inductor's interior volume, as best shown in FIG. 1B. The ultimate limitation is the S/N ratios of the impedance meter's phase detection circuit and impedance measuring circuit. Further, by varying C, measurements can be performed at a number of frequencies. This extra degree of freedom affords access to frequency dependent features of the sample. Because the present invention is inductive in nature, one might expect greater sensitivity at higher frequencies ($\Delta Z \sim (\Delta L)\omega$), a fact which is observed in experiment. Further, measurements of the change in resonant frequency upon sample removal, $\Delta f = (f_{load} - f_{empty})$, reveal progressively larger shifts for larger values of $f_0$. However, the fractional change in frequency ($\Delta f/f_0$) is actually somewhat larger at lower frequencies than at the higher frequencies.

A crucial observation of the above approach is the realization that typical lumped "L" and "R" values (from equation (3)) derived using any commercial impedance meter, must contain measurement errors. Such errors will be some composite of absolute, parasitic, temporal and statistical in nature. In a single measurement, these errors can be in the order of several percent (or more) in a typical "Z" or "$\phi$", measured at resonance. The corresponding errors in $X_2/R_2$ can be significant. However, the resonance phenomena as used in the present invention provides a unique constraining mechanism for leveraging individual data of limited accuracy into data of significantly higher quality, as will be described below.

The methodology of the present invention requires that the empty coil be re-resonated with a new capacitor, $C_0$, such as to recover the original resonant frequency, $f_0$; however, it is sometimes difficult to obtain a large enough variable capacitor to accomplish this in a typical circuit. A practical alternative is to return to the original definition of the $X_2/R_2$ as defined in equation (3). Here $L_0$ and $R_0$ refer to the unloaded coil parameters, while L' and R' refer to the loaded coil parameters, and all circuit parameters are evaluated at the original resonant frequency, $f_0$, implied by the above derivation. The empty coil is resonated with the loaded coil capacitance (C' used at $f=f_0$) and thus obtain a different frequency, $f_x$, and extrapolate the observed $L_0(f_x)$ and $R_0(f_x)$ to their respective values, $L_0(f_0)$ and $R_0(f_0)$ for $f=f_0$. Such an extrapolation is an excellent approximation for representative L and R that satisfy the phase resonant constraint equations (4). In this approximation:

$$L_0(f_0)=L_0(f_x)$$

and $$R_0(f_0)=R_0(f_x)[f_0/f_x]^{0.5} \qquad (9)$$

The last equation explicitly incorporates the "skin effect," implied by equation (8).

Figure 3:
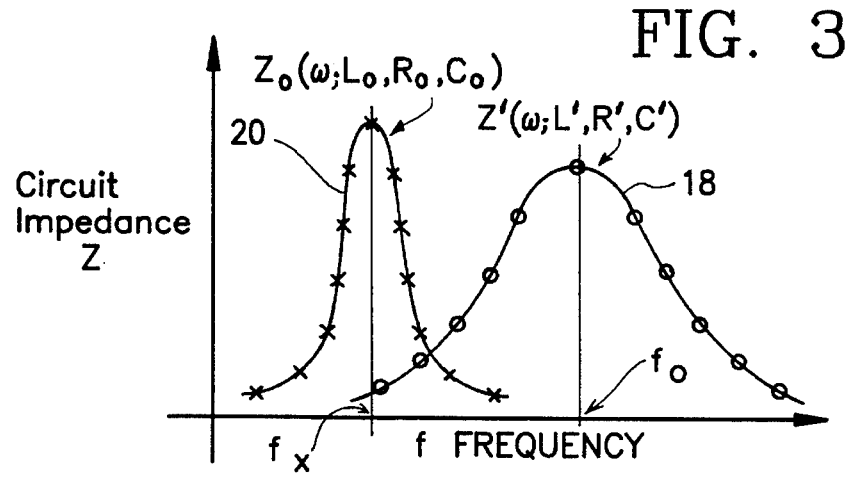
FIG. 3 is a plot of measured impedances as a function of frequency of the circuit of FIG. 1 for the unloaded and loaded conditions.

The magnitude of the impedance as a function of frequency, Z(f), for any "L-R-C" circuit can be described analytically using conventional circuit theory, and has the characteristic shape similar to that of a Lorentzian, which is peak shaped around the local resonant frequency ($f_0$, or $f_x$), as for example, shown in FIG. 3, showing curve 18 for the loaded circuit, in the case of copper for the sample material, and curve 20 for the unloaded or empty circuit. These curves create the leveraging mechanism required for the characteristic $X_2/R_2$ evaluation. The circuit impedance, Z(f), is then measured at a number of frequencies, above and below the natural resonance, for the loaded and unloaded circuits, in order to plot and sufficiently define the curves' full geometry. In doing so, this procedure considers L, R, and C as fitting parameters to be constrained by these measurements, and provides a very tight constraint as to the local values of these parameters required to generate a smooth curve containing the observed data points. Further, the values of L, R, and C rendered from this approach include all lumped and parasitic effects and thereby further increasing the intrinsic accuracy of the method. This follows in that any parasitic values, derived in this methodology, tend to be cancelled in the differential measurements implied by the execution of equation (3).

By way of an example, one might consider the case of a good conductor, such as copper. Executing the above procedure results in two ordered sets of data curves 18 and 20, similar to those portrayed in FIG. 3, and derived from frequency data scans (measurement of the impedance Z at various frequencies) so chosen as to reasonably define the curve geometry. For many elements of the periodic table, the loaded circuit curve 18: $Z=Z'(\omega; L',R',C')$ is typically positioned as shown relative to the unloaded or empty circuit curve 20: $Z=Z_0(\omega; L_0,R_0,C_0)$. However for the common ferrous group elements such as Fe, Ni, Co, Cr (and even rare earths), the relative positions may actually be reversed, although the basic curve shapes remain as shown in FIG. 3.

The generic morphology of these curves is that of the Lorentzian, and the explicit analytic form is defined by the circuit theory of the parallel "-L-R-C" circuit. After some algebra one finds that magnitude of the measured impedance, $Z(\omega)$, for this circuit is:

$$Z(\omega)=Z(\omega; L,R,C)=T(\omega)/[(1-LC\omega^2)^2+(\omega RC)^2] \qquad (10)$$

where $$T(\omega)=\{R^2+(L\omega[1-LC\omega^2]-[\omega CR^2])^2\}^{0.5}$$

Here the standard notation is used: $\omega=2\pi f$, and "f" is the frequency measured in Hertz, L is the inductance in Henrys, R is the resistance in Ohms, and C is the capacitance in Farads. The measured data of FIG. 3 in combination with Equation (10), defines a unique set of "L, R, and C" for the loaded and empty circuits, respectively. These L-R-C fitting parameters may be extracted by use of numerical techniques and render data for the loaded circuit:

$$L'=L'(f_0), R'=R'(f_0), C'=C'(f_0)$$

And for the unloaded or empty circuit:

$$L_0=L_0(f_x), R_0=R_0(f_x) \text{ and } C_0=C_0(f_x)$$

Note that $C_0$ is virtually unchanged in this procedure, apart from negligible higher order frequency attributes and is formally identical to C', a fact born out by the numerical procedure mentioned above.

These determined constants in consort with the extrapolation algorithm of Equation (9), define all the relevant observables at the given observation frequency, $f_0$, and thereby permit the quantification of the $X_2/R_2$ ratio required to complete the analyses found in Equations (6), (7) and (8).

Finally for a given measurement frequency, $f_0$, and the corresponding derived valve of $X_2/R_2$, one can constrain the values of $\mu$ and $\sigma$ through use of equations (6), (7) and (8) above. These parameters can be further resolved individually in two common limits: when $\mu=\mu_0$ (permeability of free space) and the conductivity, $\sigma$, can then be explicitly resolved to $\sigma=\sigma(f)$, or when $\sigma=\sigma_{dc}$ and the permeability, $\mu$, is then explicitly resolved as $\mu=\mu(f)$, as for the case of ferritic materials.

These equations constitute the essential experimental and (first order) analytical results embodied in the formalism of the present invention. The analytic constraints on the ratio $(a/\delta)$, that define and characterize equations (6) and (7), can be removed so as to provide a continuum solution for all $(a/\delta)$ by expanding the analytic functions required in their derivation to higher orders.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

I claim:

1. A method for quantifying the permeability of a conducting material, comprising the steps of:

a) providing a circuit including an inductor with a coil and a capacitor connected in parallel to the inductor, the coil having an interior space adapted to enclose the sample material therein;

b) inserting the sample material into the interior space of the coil to completely enclose the sample material therein;

c) resonating the circuit and the capacitor with capacitance C', at a resonant frequency $f_0$ with the sample material inserted in the coil and measuring the resulting impedance, Z' of the circuit;

d) measuring the impedance of the circuit at various frequencies above and below the resonant frequency $f_0$, and plotting a first bell-shaped curve from the measured impedances against frequencies;

e) resonating the circuit and the capacitor with capacitance C', at a resonant frequency $f_x$ with the sample material removed from the coil and measuring the resulting impedance, $Z_0$;

f) measuring the impedance of the circuit without the sample material at various frequencies above and below the resonant frequency $f_x$, and plotting a second bell-shaped curve of the measured impedances against frequencies; and g) determining the permeability of the sample material from the first and second bell-shaped curves, with $\sigma=\sigma_{dc}$.

2. A method for quantifying the conductivity of a conducting material, comprising the steps of:

a) providing a circuit including an inductor with a coil and a capacitor connected in parallel to the inductor, the coil having an interior space adapted to enclose the sample material therein;

b) inserting the sample material into the interior space of the coil to completely enclose the sample material therein;

c) resonating the circuit and the capacitor with capacitance C', at a resonant frequency $f_0$ with the sample material inserted in the coil and measuring the resulting impedance, Z' of the circuit;

d) measuring the impedance of the circuit at various frequencies above and below the resonant frequency $f_0$, and plotting a first bell-shaped curve from the measured impedances against frequencies;

e) resonating the circuit and the capacitor with capacitance C', at a resonant frequency $f_x$, with the sample material removed from the coil and measuring the resulting impedance, $Z_0$;

f) measuring the impedance of the circuit without the sample material at various frequencies above and below the resonant frequency $f_x$, and plotting a second bell-shaped curve of the measured impedances against frequencies; and g) determining the conductivity of the sample material from the first and second bell-shaped curves, with $\mu=\mu_0$.

3. A method as in claim 1, further comprising the steps of:

a) obtaining $L'(f_0)$ and $R'(f_0)$ from the first bell-shaped curve;

b) obtaining $L_0(f_x)$ and $R_0(f_x)$ from the second bell-shaped curve;

c) extrapolating $L_0(f_0)$ and $R_0(f_0)$ from the equations, $$L_o(f_o)=L_o(f_x)$$

and $$R_o(f_o)=R_o(f_x)[f_o/f_x]^{0.5}$$

d) calculating $X_2/R_2$ from the equation, $$\frac{X_2}{R_2} = \frac{\omega(L_0 - L')}{R' - R_0} ;$$

and e) calculating the permeability of the sample material from the equations, $$\frac{X_2}{R_2} = \left( \frac{\mu_0 a}{\mu \delta} - 1 \right) \text{ for } \frac{a}{\delta} > 3.6$$

$$\frac{X_2}{R_2} = \frac{4\delta^2}{a^2} \left( \frac{\delta}{a} \frac{\mu_0}{\mu} - 1 \right) + \frac{a^2}{3\delta^2} \text{ for } \frac{a}{\delta} < 1.05$$

and $$\delta = \sqrt{\frac{2}{\omega\mu\sigma}}$$

where a is the cylindrical radius and $\delta$ is the electromagnetic skin depth of a cylindrical sample material.

4. A method as in claim 2, further comprising the steps of:

a) obtaining $L'(f_0)$ and $R'(f_0)$ from the first bell-shaped curve;

b) obtaining $L_0(f_x)$ and $R_0(f_x)$ from the second bell-shaped curve;

c) extrapolating $L_0(f_0)$ and $R_0(f_0)$ from the equations, $$L_o(f_o)=L_o(f_x)$$

and $$R_o(f_o)=R_o(f_x)[f_o/f_x]^{0.5}$$

d) calculating $X_2/R_2$ from the equation, $$\frac{X_2}{R_2} = \frac{\omega(L_0 - L')}{R' - R_0} ;$$

and e) calculating the conductivity of the sample material from the equations, $$\frac{X_2}{R_2} = \left( \frac{\mu_0 a}{\mu \delta} - 1 \right) \text{ for } \frac{a}{\delta} > 3.6$$

$$\frac{X_2}{R_2} = \frac{4\delta^2}{a^2} \left( \frac{\delta}{a} \frac{\mu_0}{\mu} - 1 \right) + \frac{a^2}{3\delta^2} \text{ for } \frac{a}{\delta} < 1.05$$

and $$\delta = \sqrt{\frac{2}{\omega\mu\sigma}}$$

where a is the cylindrical radius and $\delta$ is the electromagnetic skin depth of a cylindrical sample material.

* * * * *